(12) United States Patent
Sagel

(10) Patent No.: US 9,622,840 B2
(45) Date of Patent: Apr. 18, 2017

(54) METHODS FOR WHITENING TEETH

(71) Applicant: The Procter & Gamble Company, Cincinnati, OH (US)

(72) Inventor: Paul Albert Sagel, Maineville, OH (US)

(73) Assignee: THE PROCTER & GAMBLE COMPANY, Cincinnati, OH (US)

(*) Notice: Subject to any disclaimer, the term of this patent is extended or adjusted under 35 U.S.C. 154(b) by 142 days.

(21) Appl. No.: 13/933,857

(22) Filed: Jul. 2, 2013

(65) Prior Publication Data

US 2013/0295525 A1 Nov. 7, 2013

Related U.S. Application Data

(62) Division of application No. 13/150,392, filed on Jun. 1, 2011.

(60) Provisional application No. 61/354,926, filed on Jun. 15, 2010.

(51) Int. Cl.
| | |
|---|---|
| *A61C 5/00* | (2006.01) |
| *A61C 19/06* | (2006.01) |
| *A61K 8/22* | (2006.01) |
| *A61Q 11/00* | (2006.01) |
| *A61C 1/08* | (2006.01) |

(52) U.S. Cl.
CPC ............ *A61C 19/066* (2013.01); *A61C 1/088* (2013.01); *A61K 8/22* (2013.01); *A61Q 11/00* (2013.01); *A61K 2800/81* (2013.01); *A61K 2800/87* (2013.01)

(58) Field of Classification Search
CPC .......... A61K 8/22; A61K 33/40; A61Q 11/00; A61C 19/066
USPC ..... 433/6, 29, 80, 215–216, 229; 424/49–58
See application file for complete search history.

(56) References Cited

U.S. PATENT DOCUMENTS

| | | |
|---|---|---|
| 4,290,433 A | 9/1981 | Alfano |
| 4,431,628 A | 2/1984 | Gaffar |
| RE31,815 E | 1/1985 | Alfano |
| 4,661,070 A | 4/1987 | Friedman |
| 4,668,418 A | 5/1987 | Ricchiero |
| 4,836,782 A | 6/1989 | Gonser |
| 4,840,174 A | 6/1989 | Gluckman |
| 4,877,401 A | 10/1989 | Higuchi |

(Continued)

FOREIGN PATENT DOCUMENTS

| | | |
|---|---|---|
| EP | 1 393 711 A2 | 3/2004 |
| WO | WO 98/30169 A1 | 7/1998 |

(Continued)

OTHER PUBLICATIONS

U.S. Appl. No. 13/150,392, filed Jun. 1, 2011, Paul Albert Sagel.

(Continued)

*Primary Examiner* — Matthew Nelson

(57) ABSTRACT

In a tooth whitening method, a whitening composition is applied to at least one tooth. The whitening composition is maintained on the at least one tooth for a first time period. After the first time period, a light radiation is directed toward the at least one tooth for a second time period. The first time period has a duration greater than 50% of a total duration of the first and second time periods. The whitening composition is removed from the at least one tooth.

25 Claims, 4 Drawing Sheets

(56) References Cited

U.S. PATENT DOCUMENTS

| | | |
|---|---|---|
| 4,952,143 A | 8/1990 | Becker |
| 4,980,154 A | 12/1990 | Gordon |
| 4,983,381 A | 1/1991 | Torres |
| 4,992,256 A | 2/1991 | Skaggs |
| 5,013,243 A | 5/1991 | Tanaka |
| 5,032,178 A | 7/1991 | Cornell |
| 5,037,634 A | 8/1991 | Williams |
| 5,055,048 A | 10/1991 | Vassiliadis |
| 5,114,340 A | 5/1992 | Hahn |
| 5,122,060 A | 6/1992 | Vassiliadis |
| 5,123,845 A | 6/1992 | Vassiliadis |
| 5,171,564 A | 12/1992 | Nathoo |
| 5,176,899 A | 1/1993 | Montgomery |
| 5,180,304 A | 1/1993 | Vassiliadis |
| 5,188,532 A | 2/1993 | Levy |
| RE34,196 E | 3/1993 | Munro |
| 5,232,361 A | 8/1993 | Sachdeva |
| 5,232,367 A | 8/1993 | Vassiliadis |
| 5,240,415 A | 8/1993 | Haynie |
| 5,246,019 A | 9/1993 | Godfrey |
| 5,257,931 A | 11/1993 | Pozzi |
| 5,264,205 A | 11/1993 | Kelly |
| 5,270,033 A | 12/1993 | Montgomery |
| 5,275,564 A | 1/1994 | Vassiliadis |
| 5,279,816 A | 1/1994 | Church |
| 5,281,141 A | 1/1994 | Kowalyk |
| 5,306,143 A | 4/1994 | Levy |
| 5,324,200 A | 6/1994 | Vassiliadis |
| 5,372,502 A | 12/1994 | Massen |
| 5,376,006 A | 12/1994 | Fischer |
| 5,399,088 A | 3/1995 | Mechley |
| 5,409,631 A | 4/1995 | Fischer |
| 5,424,060 A | 6/1995 | Hauschild |
| 5,429,120 A | 7/1995 | Lewitus |
| 5,433,941 A | 7/1995 | Patel |
| 5,433,956 A | 7/1995 | Patel |
| 5,456,603 A | 10/1995 | Kowalyk |
| 5,511,273 A | 4/1996 | Carroll |
| 5,575,654 A | 11/1996 | Fontenot |
| 5,586,013 A | 12/1996 | Winston |
| 5,611,793 A | 3/1997 | Wilson |
| 5,616,141 A | 4/1997 | Cipolla |
| 5,622,501 A | 4/1997 | Levy |
| 5,645,428 A | 7/1997 | Yarborough |
| 5,648,064 A | 7/1997 | Gaffar |
| 5,653,591 A | 8/1997 | Loge |
| 5,658,148 A | 8/1997 | Neuberger |
| 5,692,896 A | 12/1997 | Pospisil |
| 5,713,738 A | 2/1998 | Yarborough |
| 5,722,106 A | 3/1998 | Masterman |
| 5,746,598 A | 5/1998 | Fischer |
| 5,759,037 A | 6/1998 | Fischer |
| 5,759,038 A | 6/1998 | Fischer |
| 5,766,011 A | 6/1998 | Sibner |
| 5,770,105 A | 6/1998 | Fischer |
| 5,773,460 A | 6/1998 | Gaboury |
| 5,785,527 A | 7/1998 | Jensen |
| 5,795,153 A | 8/1998 | Rechmann |
| 5,800,165 A | 9/1998 | Kirsch |
| 5,829,448 A | 11/1998 | Fisher |
| 5,847,832 A | 12/1998 | Liskow |
| 5,851,512 A | 12/1998 | Fischer |
| 5,851,514 A | 12/1998 | Hassan |
| 5,855,870 A | 1/1999 | Fischer |
| 5,858,332 A | 1/1999 | Jensen |
| 5,879,159 A | 3/1999 | Cipolla |
| 5,879,691 A | 3/1999 | Sagel |
| 5,891,453 A | 4/1999 | Sagel |
| 5,894,620 A | 4/1999 | Polaert |
| 5,908,295 A | 6/1999 | Kawata |
| 5,908,614 A | 6/1999 | Montgomery |
| 5,921,251 A | 7/1999 | Joshi |
| 5,938,658 A | 8/1999 | Tu |
| 5,941,701 A | 8/1999 | Moran |
| 5,944,528 A | 8/1999 | Montgomery |
| 5,957,687 A | 9/1999 | Brilliant |
| 5,968,005 A | 10/1999 | Tu |
| 5,985,249 A | 11/1999 | Fischer |
| 5,998,597 A | 12/1999 | Fisher |
| 6,000,083 A | 12/1999 | Blaustein |
| 6,026,828 A | 2/2000 | Altshuler |
| 6,029,304 A | 2/2000 | Hulke |
| 6,030,222 A | 2/2000 | Tarver |
| 6,036,943 A | 3/2000 | Fischer |
| 6,056,548 A | 5/2000 | Neuberger |
| 6,074,631 A | 6/2000 | Tsuchiya |
| 6,077,073 A | 6/2000 | Jacob |
| 6,084,242 A | 7/2000 | Brown |
| 6,086,363 A | 7/2000 | Moran |
| 6,086,365 A | 7/2000 | Fields |
| 6,086,855 A | 7/2000 | Fischer |
| 6,089,740 A | 7/2000 | Forehand |
| 6,094,767 A | 8/2000 | Iimura |
| 6,102,696 A | 8/2000 | Osterwalder |
| 6,106,293 A | 8/2000 | Wiesel |
| 6,108,850 A | 8/2000 | McLaughlin |
| 6,116,900 A | 9/2000 | Ostler |
| 6,135,126 A | 10/2000 | Joshi |
| 6,136,297 A * | 10/2000 | Sagel .................. A61K 8/0208 106/35 |
| 6,149,895 A | 11/2000 | Kutsch |
| 6,162,055 A | 12/2000 | Montgomery |
| 6,190,170 B1 | 2/2001 | Morris |
| 6,221,341 B1 | 4/2001 | Montgomery |
| 6,231,343 B1 | 5/2001 | Ishibashi |
| 6,234,793 B1 | 5/2001 | Brattesani |
| 6,254,388 B1 | 7/2001 | Yarborough |
| 6,276,933 B1 | 8/2001 | Melnyk |
| 6,281,265 B1 | 8/2001 | Montgomery |
| 6,287,120 B1 * | 9/2001 | Wiesel ................ A61C 19/066 433/215 |
| 6,290,496 B1 | 9/2001 | Azar |
| 6,312,671 B1 | 11/2001 | Jensen |
| 6,318,996 B1 | 11/2001 | Melikechi |
| 6,322,774 B1 | 11/2001 | Jensen |
| 6,328,567 B1 | 12/2001 | Morris |
| 6,331,113 B1 | 12/2001 | Morris |
| 6,340,301 B2 | 1/2002 | Darnell |
| 6,343,400 B1 | 2/2002 | Massholder |
| 6,343,933 B1 | 2/2002 | Montgomery |
| 6,350,123 B1 | 2/2002 | Rizoiu |
| 6,361,320 B2 | 3/2002 | Yarborough |
| 6,364,665 B1 | 4/2002 | Trettenero |
| 6,365,132 B1 | 4/2002 | Litkowski |
| 6,379,376 B1 | 4/2002 | Lubart |
| 6,384,917 B1 | 5/2002 | Radkin |
| 6,387,353 B1 | 5/2002 | Jensen |
| 6,391,281 B1 | 5/2002 | Rueggeberg |
| 6,391,283 B1 | 5/2002 | Jensen |
| 6,416,319 B1 * | 7/2002 | Cipolla .................... A61C 5/00 433/215 |
| 6,419,483 B1 | 7/2002 | Adam |
| 6,422,868 B1 | 7/2002 | Lindquist |
| 6,439,888 B1 | 8/2002 | Boutoussov |
| 6,447,757 B1 | 9/2002 | Orlowski |
| 6,468,077 B1 | 10/2002 | Melikechi |
| 6,471,716 B1 | 10/2002 | Pecukonis |
| 6,475,469 B1 | 11/2002 | Montgomery |
| 6,479,037 B1 | 11/2002 | Montgomery |
| 6,485,300 B1 | 11/2002 | Muller |
| 6,488,914 B2 | 12/2002 | Montgomery |
| 6,493,570 B1 | 12/2002 | Dees |
| 6,496,998 B2 | 12/2002 | Moran |
| 6,497,575 B2 | 12/2002 | Zavitsanos |
| 6,500,408 B2 | 12/2002 | Chen |
| 6,503,485 B1 | 1/2003 | Allred |
| 6,511,317 B2 | 1/2003 | Melikechi |
| 6,514,075 B1 | 2/2003 | Jacob |
| 6,533,582 B2 | 3/2003 | Lindquist |
| 6,534,043 B2 | 3/2003 | Ryles |
| 6,536,628 B2 | 3/2003 | Montgomery |
| 6,537,305 B1 | 3/2003 | Thiberg |
| 6,551,808 B2 | 4/2003 | Jackson |
| 6,558,653 B2 | 5/2003 | Andersen |

(56) References Cited

U.S. PATENT DOCUMENTS

| | | | |
|---|---|---|---|
| 6,561,803 B1 | 5/2003 | Rizoiu | |
| 6,576,227 B1 | 6/2003 | Montgomery | |
| 6,592,851 B2 | 7/2003 | Warford | |
| 6,613,359 B2 | 9/2003 | Victor | |
| 6,616,447 B1 | 9/2003 | Rizoiu | |
| 6,616,451 B1 | 9/2003 | Rizolu | |
| 6,623,272 B2 | 9/2003 | Clemans | |
| 6,663,659 B2 | 12/2003 | McDaniel | |
| 6,685,471 B1 | 2/2004 | Kawamura | |
| 6,686,193 B2 | 2/2004 | Maher | |
| 6,702,576 B2 | 3/2004 | Fischer | |
| 6,703,007 B2 | 3/2004 | Glenn | |
| 6,724,522 B2 | 4/2004 | Hartung | |
| 6,730,316 B2 | 5/2004 | Chen | |
| 6,733,290 B2 | 5/2004 | West | |
| 6,746,664 B2 | 6/2004 | Allred | |
| 6,746,679 B2 | 6/2004 | Nathoo | |
| 6,764,309 B2 | 7/2004 | Cozean | |
| 6,769,911 B2 | 8/2004 | Buchalla | |
| 6,783,363 B2 | 8/2004 | Eguchi | |
| 6,793,489 B2 | 9/2004 | Morris | |
| 6,808,722 B2 | 10/2004 | Victor | |
| 6,824,704 B2 | 11/2004 | Chadwick | |
| 6,843,981 B1 | 1/2005 | Ishibashi et al. | |
| 6,846,182 B1 | 1/2005 | Sibner | |
| 6,886,208 B2 | 5/2005 | Kemp et al. | |
| 6,893,259 B1 | 5/2005 | Reizenson | |
| 6,902,397 B2 | 6/2005 | Farrell et al. | |
| 6,923,761 B1 | 8/2005 | Dorfman | |
| 6,933,327 B2 | 8/2005 | Yamakawa | |
| 6,939,535 B2 | 9/2005 | Cozean | |
| 6,945,777 B2 | 9/2005 | Black | |
| 6,946,098 B2 | 9/2005 | Miekka | |
| 6,946,147 B2 | 9/2005 | Victor | |
| 6,949,240 B2 * | 9/2005 | Sagel | A61K 8/0208 424/401 |
| 6,951,463 B2 | 10/2005 | Masuhara | |
| 6,952,856 B2 | 10/2005 | Kaizuka | |
| 6,955,639 B2 | 10/2005 | Hainfeld | |
| 6,957,907 B2 | 10/2005 | Fischer | |
| 6,958,144 B2 | 10/2005 | Montgomery | |
| 6,964,567 B2 | 11/2005 | Kerschbaumer | |
| 6,974,224 B2 | 12/2005 | Thomas Benedict | |
| 6,976,841 B1 | 12/2005 | Osterwalder | |
| 6,981,870 B2 | 1/2006 | Heasley | |
| 6,981,874 B2 | 1/2006 | Allred | |
| 6,986,883 B2 | 1/2006 | Pellico | |
| 6,988,893 B2 | 1/2006 | Haywood | |
| 7,018,622 B2 | 3/2006 | Goodhart | |
| 7,025,950 B2 | 4/2006 | Majeti | |
| 7,035,702 B2 | 4/2006 | Jelonek | |
| 7,048,731 B2 | 5/2006 | Altshuler | |
| 7,060,256 B2 | 6/2006 | Pellico | |
| 7,086,862 B2 | 8/2006 | Craig | |
| 7,090,497 B1 | 8/2006 | Harris | |
| 7,094,057 B2 | 8/2006 | Friedman | |
| 7,094,393 B2 | 8/2006 | Montgomery | |
| 7,097,449 B2 | 8/2006 | Jessop | |
| 7,101,384 B2 | 9/2006 | Benedict | |
| 7,104,792 B2 | 9/2006 | Taub | |
| 7,107,996 B2 | 9/2006 | Ganz | |
| 7,144,248 B2 | 12/2006 | Irwin | |
| 7,144,249 B2 | 12/2006 | Rizoiu | |
| 7,153,015 B2 | 12/2006 | Brukilacchio | |
| 7,156,656 B2 | 1/2007 | Duret | |
| 7,160,111 B2 | 1/2007 | Baughman | |
| 7,163,318 B2 | 1/2007 | Panagotacos | |
| 7,163,400 B2 | 1/2007 | Cozean | |
| 7,189,385 B2 | 3/2007 | Montgomery | |
| 7,201,578 B2 | 4/2007 | Yarborough | |
| 7,201,767 B2 | 4/2007 | Bhullar | |
| D542,947 S | 5/2007 | Rose | |
| 7,210,814 B2 | 5/2007 | Scott | |
| 7,214,262 B2 | 5/2007 | Hurwitz | |
| 7,223,270 B2 | 5/2007 | Altshuler | |
| 7,223,281 B2 | 5/2007 | Altshuler | |
| 7,250,155 B2 | 7/2007 | Yamaguchi | |
| 7,261,558 B2 | 8/2007 | Rizoiu | |
| 7,269,873 B2 | 9/2007 | Brewer | |
| 7,287,981 B2 | 10/2007 | Hirsch | |
| 7,292,759 B2 | 11/2007 | Boutoussov | |
| 7,292,907 B2 | 11/2007 | Whaite | |
| 7,296,318 B2 | 11/2007 | Mourad | |
| 7,300,175 B2 | 11/2007 | Brukilacchio | |
| 7,319,529 B2 | 1/2008 | Babayoff | |
| 7,320,594 B1 | 1/2008 | Rizoiu | |
| 7,320,595 B2 | 1/2008 | Duret | |
| 7,324,661 B2 | 1/2008 | Kemp | |
| 7,328,708 B2 | 2/2008 | Malak | |
| 7,329,273 B2 | 2/2008 | Altshuler | |
| 7,329,274 B2 | 2/2008 | Altshuler | |
| 7,331,784 B2 | 2/2008 | Suzuki | |
| 7,335,025 B2 | 2/2008 | Levine | |
| 7,354,269 B2 | 4/2008 | Duret | |
| 7,354,448 B2 * | 4/2008 | Altshuler | A46B 15/0002 128/898 |
| 7,367,934 B2 | 5/2008 | Hainfeld | |
| 7,402,299 B2 | 7/2008 | Dees | |
| 7,410,283 B2 | 8/2008 | West | |
| 7,422,598 B2 | 9/2008 | Altshuler | |
| 7,445,448 B2 | 11/2008 | Haisch | |
| 7,448,109 B2 | 11/2008 | Brewer | |
| 7,464,715 B1 | 12/2008 | Husted | |
| 7,488,088 B2 | 2/2009 | Brukilacchio | |
| 7,488,101 B2 | 2/2009 | Brukilacchio | |
| 7,499,760 B2 | 3/2009 | Rose | |
| 7,511,829 B2 | 3/2009 | Babayoff | |
| 7,530,940 B2 | 5/2009 | Hainfeld | |
| 7,550,419 B2 | 6/2009 | Fütterer | |
| 7,563,095 B2 | 7/2009 | Morris | |
| 7,568,579 B2 | 8/2009 | Moore | |
| 7,577,284 B2 | 8/2009 | Wong | |
| 7,581,846 B2 | 9/2009 | Hayman | |
| 7,581,864 B2 | 9/2009 | Craig | |
| 7,596,253 B2 | 9/2009 | Wong | |
| 7,602,301 B1 | 10/2009 | Stirling | |
| 7,612,045 B2 | 11/2009 | Eldridge | |
| 7,621,746 B2 | 11/2009 | Baughman | |
| 7,641,892 B2 | 1/2010 | Gebreselassie | |
| 7,645,137 B2 | 1/2010 | Wasyluch | |
| 7,668,355 B2 | 2/2010 | Wong | |
| 7,683,103 B2 | 3/2010 | Sawada | |
| 7,702,139 B2 | 4/2010 | Liang | |
| 7,704,754 B2 | 4/2010 | Malak | |
| 7,724,378 B2 | 5/2010 | Babayoff | |
| 7,743,447 B2 | 6/2010 | Kemp | |
| 7,748,072 B2 | 7/2010 | Rycroft | |
| 7,768,685 B2 | 8/2010 | Hoshino | |
| 7,790,073 B2 | 9/2010 | Culp | |
| 7,802,988 B2 | 9/2010 | Yarborough | |
| 7,813,787 B2 | 10/2010 | De Josselin De Jong | |
| 7,813,790 B2 | 10/2010 | De Josselin De Jong | |
| 7,815,434 B2 | 10/2010 | Takei | |
| 7,891,361 B2 | 2/2011 | Irwin | |
| 2001/0002994 A1 | 6/2001 | Masuhara | |
| 2001/0021374 A1 | 9/2001 | Montgomery | |
| 2001/0046655 A1 | 11/2001 | Yarborough | |
| 2001/0056133 A1 | 12/2001 | Montgomery | |
| 2002/0041855 A1 | 4/2002 | Glenn | |
| 2002/0119100 A1 | 8/2002 | Okada | |
| 2002/0137001 A1 | 9/2002 | Cipolla | |
| 2002/0137728 A1 | 9/2002 | Montgomery | |
| 2002/0141950 A1 | 10/2002 | Chen | |
| 2002/0141951 A1 | 10/2002 | Montgomery | |
| 2002/0155070 A1 | 10/2002 | Chen | |
| 2002/0155071 A1 | 10/2002 | McLaughlin | |
| 2002/0172919 A1 | 11/2002 | Zavitsanos | |
| 2002/0176827 A1 * | 11/2002 | Rajaiah | A61C 19/063 424/49 |
| 2002/0187455 A1 | 12/2002 | Melikechi | |
| 2002/0192248 A1 | 12/2002 | Victor | |
| 2002/0192260 A1 | 12/2002 | Victor | |
| 2003/0003421 A1 | 1/2003 | Bestenheider | |
| 2003/0012746 A1 | 1/2003 | Chen | |

(56) References Cited

U.S. PATENT DOCUMENTS

| | | |
|---|---|---|
| 2003/0017435 A1 | 1/2003 | Ibsen |
| 2003/0031555 A1 | 2/2003 | Noe |
| 2003/0036031 A1 | 2/2003 | Lieb |
| 2003/0036037 A1 | 2/2003 | Zavitsanos |
| 2003/0036582 A1 | 2/2003 | Yamakawa |
| 2003/0044361 A1 | 3/2003 | Chen |
| 2003/0054990 A1 | 3/2003 | Averback |
| 2003/0059381 A1* | 3/2003 | Goodhart ............ A61C 19/063 424/53 |
| 2003/0072722 A1 | 4/2003 | Nathoo |
| 2003/0082115 A1 | 5/2003 | Allred |
| 2003/0089886 A1 | 5/2003 | Montgomery |
| 2003/0091954 A1 | 5/2003 | West |
| 2003/0104022 A1 | 6/2003 | Victor |
| 2003/0104340 A1 | 6/2003 | Clemans |
| 2003/0104341 A1 | 6/2003 | Zavitsanos |
| 2003/0147821 A1 | 8/2003 | Victor |
| 2003/0152528 A1 | 8/2003 | Singh |
| 2003/0170189 A1 | 9/2003 | Victor |
| 2003/0180690 A1 | 9/2003 | Neuberger |
| 2003/0190293 A1 | 10/2003 | Pellico |
| 2003/0198605 A1 | 10/2003 | Montgomery |
| 2003/0211051 A1 | 11/2003 | Majeti |
| 2003/0220416 A1 | 11/2003 | Montgomery |
| 2004/0019990 A1 | 2/2004 | Farrell |
| 2004/0023184 A1 | 2/2004 | De Josselin De Jong |
| 2004/0047816 A1 | 3/2004 | Yamaguchi |
| 2004/0052798 A1 | 3/2004 | Neuberger |
| 2004/0091834 A1 | 5/2004 | Rizoiu |
| 2004/0101497 A1 | 5/2004 | Montgomery |
| 2004/0106082 A1 | 6/2004 | Rizoiu |
| 2004/0109829 A1 | 6/2004 | Nonami |
| 2004/0110111 A1 | 6/2004 | Wasylucha |
| 2004/0136002 A1 | 7/2004 | Whaite |
| 2004/0141336 A1 | 7/2004 | West |
| 2004/0146467 A1 | 7/2004 | Pellico |
| 2004/0151691 A1 | 8/2004 | Oxman |
| 2004/0152051 A1 | 8/2004 | Craig |
| 2004/0162596 A1 | 8/2004 | Altshuler |
| 2004/0170578 A1 | 9/2004 | Sugihara |
| 2004/0191729 A1 | 9/2004 | Altshuler |
| 2004/0193235 A1 | 9/2004 | Altshuler |
| 2004/0193236 A1 | 9/2004 | Altshuler |
| 2004/0199227 A1 | 10/2004 | Altshuler |
| 2004/0201980 A1 | 10/2004 | Fischer |
| 2004/0210276 A1 | 10/2004 | Altshuler |
| 2004/0234460 A1 | 11/2004 | Tarver et al. |
| 2004/0240716 A1 | 12/2004 | De Josselin De Jong |
| 2004/0248058 A1 | 12/2004 | Hahn |
| 2004/0254478 A1 | 12/2004 | de Josselin de Jong et al. |
| 2004/0258723 A1* | 12/2004 | Singh ................ A61C 19/063 424/401 |
| 2004/0259053 A1 | 12/2004 | Bekov |
| 2004/0265244 A1 | 12/2004 | Rosen |
| 2005/0008584 A1 | 1/2005 | Montgomery |
| 2005/0019276 A1 | 1/2005 | Nathoo |
| 2005/0026103 A1* | 2/2005 | Wasylucha ............ A61C 3/005 433/29 |
| 2005/0026107 A1 | 2/2005 | Mongtomery |
| 2005/0048434 A1 | 3/2005 | Cipolla |
| 2005/0048444 A1 | 3/2005 | Creamer |
| 2005/0050658 A1 | 3/2005 | Chan |
| 2005/0053895 A1 | 3/2005 | Pinyayev |
| 2005/0053896 A1 | 3/2005 | Pinyayev |
| 2005/0053898 A1 | 3/2005 | Ghosh |
| 2005/0064371 A1 | 3/2005 | Soukos |
| 2005/0074723 A1 | 4/2005 | Ostler et al. |
| 2005/0084825 A1 | 4/2005 | Yarborough |
| 2005/0084826 A1 | 4/2005 | Pilaro et al. |
| 2005/0107849 A1 | 5/2005 | Altshuler |
| 2005/0123877 A1 | 6/2005 | Duret et al. |
| 2005/0130253 A1 | 6/2005 | Lye |
| 2005/0134576 A1 | 6/2005 | Lin |
| 2005/0144029 A1 | 6/2005 | Rakowski |
| 2005/0164169 A1 | 7/2005 | Malak |
| 2005/0170316 A1 | 8/2005 | Russell |
| 2005/0172429 A1 | 8/2005 | Russell et al. |
| 2005/0175956 A1 | 8/2005 | Russell |
| 2005/0175959 A1 | 8/2005 | Jodaikin |
| 2005/0183221 A1 | 8/2005 | Kemp |
| 2005/0196721 A1 | 9/2005 | Jackson |
| 2005/0202363 A1 | 9/2005 | Osterwalder |
| 2005/0207976 A1 | 9/2005 | Dees |
| 2005/0221251 A1 | 10/2005 | Soukos |
| 2005/0244794 A1 | 11/2005 | Kemp |
| 2005/0255053 A1 | 11/2005 | Cozean |
| 2005/0256554 A1 | 11/2005 | Malak |
| 2005/0265933 A1 | 12/2005 | Montgomery |
| 2005/0271997 A1 | 12/2005 | Mikami |
| 2005/0281887 A1 | 12/2005 | Rizoiu |
| 2005/0282889 A1 | 12/2005 | Dees |
| 2006/0001739 A1 | 1/2006 | Babayoff |
| 2006/0003284 A1 | 1/2006 | Sale |
| 2006/0004306 A1 | 1/2006 | Altshuler |
| 2006/0008767 A1 | 1/2006 | Whalen |
| 2006/0019214 A1 | 1/2006 | Lawrence |
| 2006/0019220 A1 | 1/2006 | Loebel |
| 2006/0020309 A1 | 1/2006 | Altshuler |
| 2006/0029901 A1 | 2/2006 | Rose |
| 2006/0029902 A1 | 2/2006 | Rose |
| 2006/0034780 A1 | 2/2006 | Guan |
| 2006/0040231 A1 | 2/2006 | Quan |
| 2006/0057537 A1 | 3/2006 | Tamburrino |
| 2006/0063853 A1 | 3/2006 | Hurwitz |
| 2006/0063979 A1 | 3/2006 | Rosenblood |
| 2006/0078510 A1 | 4/2006 | Takeiu |
| 2006/0084028 A1 | 4/2006 | Cheetham |
| 2006/0085052 A1 | 4/2006 | Feuerstein |
| 2006/0093561 A1 | 5/2006 | Kennedy |
| 2006/0099153 A1 | 5/2006 | Kato |
| 2006/0099155 A1 | 5/2006 | MacDonald |
| 2006/0099156 A1 | 5/2006 | MacDonald |
| 2006/0104922 A1 | 5/2006 | Tarver |
| 2006/0110700 A1 | 5/2006 | Cipolla |
| 2006/0110701 A1 | 5/2006 | Cwik |
| 2006/0116669 A1 | 6/2006 | Dolleris |
| 2006/0127837 A1 | 6/2006 | Nguyen |
| 2006/0127862 A1 | 6/2006 | Kakuda |
| 2006/0141422 A1 | 6/2006 | K. Philp |
| 2006/0183081 A1 | 8/2006 | Bevilacqua |
| 2006/0188835 A1 | 8/2006 | Nagel |
| 2006/0194172 A1 | 8/2006 | Loveridge |
| 2006/0198796 A1 | 9/2006 | Giniger |
| 2006/0198797 A1 | 9/2006 | Giniger |
| 2006/0199859 A1 | 9/2006 | Dees |
| 2006/0204453 A1 | 9/2006 | Giniger |
| 2006/0222600 A1 | 10/2006 | Pinyayev |
| 2006/0222604 A1 | 10/2006 | Yamaguchi |
| 2006/0223024 A1 | 10/2006 | Hochman |
| 2006/0234189 A1 | 10/2006 | Duret |
| 2006/0240375 A1 | 10/2006 | Soukos |
| 2006/0240377 A1 | 10/2006 | De Josselin De Jong |
| 2006/0240381 A1 | 10/2006 | Rizoiu |
| 2006/0240386 A1 | 10/2006 | Yaniv |
| 2006/0245187 A1 | 11/2006 | Scott |
| 2006/0251591 A1 | 11/2006 | Montgomery |
| 2006/0253176 A1 | 11/2006 | Caruso |
| 2006/0257822 A1* | 11/2006 | Ghosh ................ A46B 15/0036 433/215 |
| 2006/0269897 A1 | 11/2006 | Gill |
| 2006/0280696 A1 | 12/2006 | Jensen |
| 2006/0292182 A1 | 12/2006 | Kemeny |
| 2007/0003905 A1 | 1/2007 | Nguyen |
| 2007/0010575 A1 | 1/2007 | Dees |
| 2007/0011836 A1 | 1/2007 | Brewer |
| 2007/0015112 A1 | 1/2007 | Hochman |
| 2007/0020584 A1 | 1/2007 | Madray |
| 2007/0021640 A1 | 1/2007 | Perez |
| 2007/0037113 A1 | 2/2007 | Scott |
| 2007/0037126 A1 | 2/2007 | Craig |
| 2007/0039109 A1 | 2/2007 | Nandat |
| 2007/0053200 A1 | 3/2007 | Brukilacchio |
| 2007/0054234 A1 | 3/2007 | Oxman |
| 2007/0054236 A1 | 3/2007 | Rizoiu |

(56) References Cited

U.S. PATENT DOCUMENTS

| | | |
|---|---|---|
| 2007/0058389 A1 | 3/2007 | Brukilacchio |
| 2007/0059660 A1 | 3/2007 | Rizoiu |
| 2007/0099154 A1 | 5/2007 | Johnson |
| 2007/0105063 A1 | 5/2007 | Pinyayev |
| 2007/0111166 A1 | 5/2007 | Dursi |
| 2007/0111167 A1 | 5/2007 | Russell |
| 2007/0122769 A1 | 5/2007 | Levine |
| 2007/0128132 A1 | 6/2007 | Piergallini |
| 2007/0148612 A1 | 6/2007 | Massad |
| 2007/0154863 A1 | 7/2007 | Cai |
| 2007/0160958 A1 | 7/2007 | Belikov |
| 2007/0207442 A1 | 9/2007 | Yarborough |
| 2007/0224570 A1 | 9/2007 | West |
| 2007/0231773 A1 | 10/2007 | Pontynen |
| 2007/0237727 A1 | 10/2007 | Matthews |
| 2007/0237728 A1 | 10/2007 | Verheyen |
| 2007/0248930 A1 | 10/2007 | Brawn |
| 2007/0253918 A1 | 11/2007 | Campanale |
| 2007/0259310 A1 | 11/2007 | Goodson |
| 2007/0264608 A1 | 11/2007 | Brosnihan |
| 2007/0298372 A1* | 12/2007 | Pinyayev ............... A61C 17/22 433/29 |
| 2008/0024768 A1 | 1/2008 | Babayoff |
| 2008/0025013 A1 | 1/2008 | Lockamy |
| 2008/0031960 A1 | 2/2008 | Wilson |
| 2008/0032252 A1 | 2/2008 | Hayman |
| 2008/0032253 A1 | 2/2008 | Montgomery |
| 2008/0038686 A1 | 2/2008 | Nagai |
| 2008/0039592 A1 | 2/2008 | Sawada |
| 2008/0044363 A1 | 2/2008 | Montgomery |
| 2008/0044796 A1 | 2/2008 | Hsu |
| 2008/0050408 A1 | 2/2008 | Hayman |
| 2008/0050448 A1 | 2/2008 | Wilson |
| 2008/0057469 A1 | 3/2008 | Hayman |
| 2008/0063612 A1 | 3/2008 | MacDonald |
| 2008/0063999 A1 | 3/2008 | Osborn |
| 2008/0064001 A1 | 3/2008 | Dorfman |
| 2008/0069781 A1 | 3/2008 | Neuberger |
| 2008/0075676 A1 | 3/2008 | MacDonald |
| 2008/0090198 A1 | 4/2008 | Liang |
| 2008/0096156 A1 | 4/2008 | Rose |
| 2008/0096157 A1 | 4/2008 | Ziemba |
| 2008/0101073 A1 | 5/2008 | Hayman |
| 2008/0109973 A1 | 5/2008 | Farrell |
| 2008/0112903 A1 | 5/2008 | Montgomery |
| 2008/0118886 A1 | 5/2008 | Liang |
| 2008/0124671 A1 | 5/2008 | Nguyen |
| 2008/0131843 A1 | 6/2008 | Montgomery |
| 2008/0132587 A1 | 6/2008 | Montgomery |
| 2008/0138764 A1 | 6/2008 | Rizoiu |
| 2008/0138770 A1 | 6/2008 | Montgomery |
| 2008/0145389 A1 | 6/2008 | Montgomery |
| 2008/0214530 A1 | 9/2008 | Colles |
| 2008/0233541 A1 | 9/2008 | De Vreese |
| 2008/0246000 A1 | 10/2008 | Sakaguchi |
| 2008/0254405 A1* | 10/2008 | Montgomery ......... A61C 19/06 433/29 |
| 2008/0255549 A1 | 10/2008 | Rose |
| 2008/0260660 A1 | 10/2008 | Engelbrecht |
| 2008/0274066 A1 | 11/2008 | Montgomery |
| 2008/0285302 A1 | 11/2008 | Scott |
| 2008/0311545 A1 | 12/2008 | Ostler |
| 2009/0017416 A1 | 1/2009 | Nguyen |
| 2009/0029311 A1 | 1/2009 | Chan |
| 2009/0035725 A1 | 2/2009 | Loebel |
| 2009/0046476 A1 | 2/2009 | West |
| 2009/0068613 A1 | 3/2009 | Wang |
| 2009/0081136 A1* | 3/2009 | Sharma ............... A61K 8/0295 424/53 |
| 2009/0081611 A1 | 3/2009 | Hines |
| 2009/0091913 A1 | 4/2009 | Li |
| 2009/0092643 A1 | 4/2009 | De Vreese |
| 2009/0111878 A1 | 4/2009 | Kawabata |
| 2009/0142724 A1 | 6/2009 | Rosenblood |
| 2009/0148808 A1 | 6/2009 | Alexander |
| 2009/0148815 A1 | 6/2009 | Philp |
| 2009/0155740 A1 | 6/2009 | Jensen |
| 2009/0162810 A1 | 6/2009 | Werner |
| 2009/0175917 A1 | 7/2009 | Engelbrecht |
| 2009/0191504 A1 | 7/2009 | Mannino |
| 2009/0191511 A1 | 7/2009 | Yarovesky |
| 2009/0208543 A1 | 8/2009 | Nathoo |
| 2009/0208894 A1 | 8/2009 | Orloff |
| 2009/0210032 A1 | 8/2009 | Beiski |
| 2009/0214448 A1* | 8/2009 | Sagel ................ A61C 19/063 424/53 |
| 2009/0220919 A1 | 9/2009 | Yang |
| 2009/0238778 A1 | 9/2009 | Mordas |
| 2009/0285766 A1 | 11/2009 | Kishen |
| 2010/0028829 A1* | 2/2010 | Lewis ................ A61C 19/066 433/80 |
| 2010/0040565 A1 | 2/2010 | Homola |
| 2010/0092407 A1 | 4/2010 | Kurata |
| 2010/0098733 A1 | 4/2010 | Stasko |
| 2010/0100030 A1 | 4/2010 | Driscoll |
| 2010/0112510 A1 | 5/2010 | Wasylucha |
| 2010/0112526 A1 | 5/2010 | Keller |
| 2010/0119989 A1 | 5/2010 | Raybuck |
| 2010/0136498 A1 | 6/2010 | Baughman |
| 2010/0143857 A1 | 6/2010 | Colles |
| 2010/0151406 A1 | 6/2010 | Boutoussov |
| 2010/0151407 A1 | 6/2010 | Rizoiu |
| 2010/0158960 A1 | 6/2010 | Chandra |
| 2010/0167226 A1 | 7/2010 | Altshuler |
| 2010/0167227 A1 | 7/2010 | Jun |
| 2010/0172846 A1 | 7/2010 | Matthews |
| 2010/0179469 A1 | 7/2010 | Hammond |
| 2010/0196857 A1 | 8/2010 | Yarborough |
| 2010/0203465 A1 | 8/2010 | Bria |
| 2010/0208275 A1 | 8/2010 | Babayoff |
| 2010/0233022 A1 | 9/2010 | Street |
| 2010/0239998 A1 | 9/2010 | Snyder |
| 2010/0266989 A1* | 10/2010 | Piergallini ............... A61K 8/22 433/215 |
| 2010/0266990 A1 | 10/2010 | Cooley |
| 2011/0027384 A1 | 2/2011 | Kishen |
| 2011/0054574 A1 | 3/2011 | Felix |

FOREIGN PATENT DOCUMENTS

| | | |
|---|---|---|
| WO | WO 99/40870 A1 | 8/1999 |
| WO | WO 2007/080453 A2 | 7/2007 |

OTHER PUBLICATIONS

International Search Report and Written Opinion for PCT/US2011/039399, Oct. 17, 2011.

* cited by examiner

METHODS FOR WHITENING TEETH

CROSS REFERENCE TO RELATED APPLICATION

This application claims priority to provisional U.S. App. No. 61/354,926 filed Jun. 15, 2010, the substance of which is incorporated herein by reference.

FIELD

This application relates to tooth whitening compositions, products, devices, and methods.

BACKGROUND

Many approaches are used to whiten teeth. One common approach uses abrasives (for example, in toothpastes and prophyaxis pastes) in combination with a polishing action to polish discolorations and stains off of the surface of the teeth. Because abrasives only work on the surface of the teeth, the intrinsic color of the teeth is largely unchanged. As such, abrasives only offer limited effectiveness in whitening of the teeth.

Another approach is the use of chemical whitening actives in a composition to intrinsically and extrinsically whiten teeth. A chemical whitening active is applied to the teeth for a period of time to allow the active to act upon the teeth and provide an improvement in the whiteness of the teeth. Whiteners are commonly applied to the teeth using toothpastes, rinses, gums, floss, tablets, strips and trays. A common chemical whitening active is peroxide. Often, strips and trays are used to apply peroxide for contact times beyond that achievable with typical toothbrushing. Concentration of the whitening active, contact time and number of applications are some of the primary parameters which dictate the rate and amount of whitening achieved with peroxide based tooth whitening compositions. Whitening products using a strip of material in combination with a chemical whitening active are described, for example, in U.S. Pat. Nos. 5,891,453 and 5,879,691, the disclosures of which are incorporated herein by reference. The whitening composition described therein can include a peroxide active.

Efforts to increase the whitening efficacy of products in order to deliver a more satisfying product experience have included increasing the concentration of peroxide for a faster whitening per time of use. Maintaining the peroxide on the tooth surface for longer contact times and/or for an increased number or frequency of applications have also been employed for increased whitening. While increasing concentration, increasing wear time and increasing number of applications can be effective methods of achieving higher degrees of tooth whitening from a tooth whitening product, each of these parameters also may have a negative impact on the consumer's experience.

Increasing the concentration of the peroxide in the whitening composition, holding all other parameters essentially constant, can produce more tooth sensitivity and cause more soft tissue irritation. Sufficiently high concentrations of peroxide may require a physical barrier, such as a rubber dam, to prevent the peroxide from contacting and burning the soft tissue thereby making the use of the high peroxide concentrations inconvenient and impractical for unsupervised at home and repeated use. In fact, even conventional in-office tooth whitening compositions having a peroxide concentration equivalent to as low as 13% hydrogen peroxide, often utilize a rubber dam to protect the soft tissue during the bleaching process. Increasing the use time and/or frequency generally increases the amount of tooth sensitivity and gingival irritation as well as make the product more inconvenient to use.

SUMMARY

The present application describes a method for whitening teeth using light radiation to photochemically activate a tooth stain for enhanced whitening by a bleaching or oxidizing agent.

Accordingly, in an exemplary tooth whitening method of the present application, a whitening composition is applied to at least one tooth. The whitening composition is maintained on the at least one tooth for a first time period. After the first time period, a light radiation is directed toward the at least one tooth for a second time period. The first time period has a duration greater than about 50% of a total duration of the first and second time periods. The whitening composition is removed from the at least one tooth before, during, or after the second time period.

In accordance with another aspect of the present application, an exemplary light enhanced tooth whitening kit includes a strip sized to cover one or more teeth, with the strip including a layer of a tooth whitening composition. The kit further includes a portable light source configured to emit light radiation having an intensity of no greater than about 150 mW/cm$^2$.

BRIEF DESCRIPTION OF THE DRAWINGS

Further features and advantages of the invention will become apparent from the following detailed description made with reference to the accompanying drawings, wherein.

DETAILED DESCRIPTION

Figure 1:
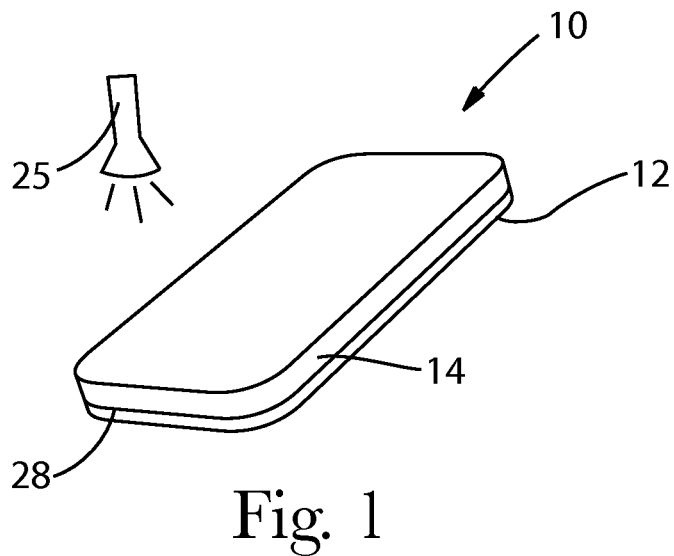
FIG. 1 illustrates a light enhanced tooth whitening kit.

This Detailed Description merely describes embodiments of the invention and is not intended to limit the scope of the claims in any way. Indeed, the invention as claimed is broader than and unlimited by the preferred embodiments, and the terms used in the claims have their full ordinary meaning.

Also, while the exemplary embodiments described in the specification and illustrated in the drawings relate to methods of whitening teeth involving treatment with a tooth whitening composition including a peroxide active, it should be understood that many of the inventive aspects described herein may be applied to other tooth whitening methods, including for example methods involving the use of other tooth whitening compositions.

Figure 4:
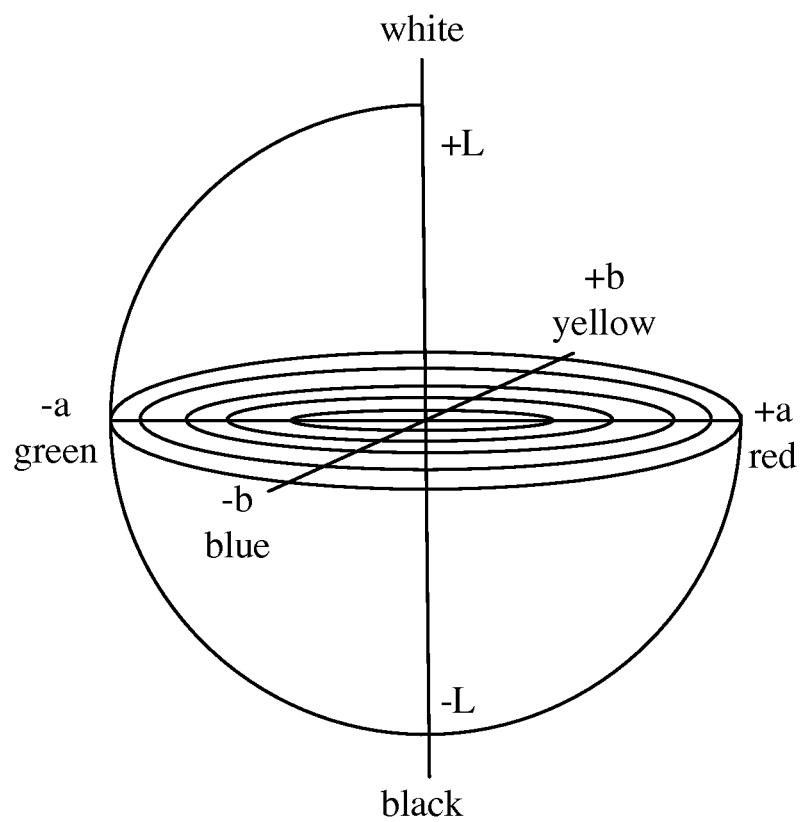
FIG. 4 is a schematic illustration of the 1976 CIE LAB color space.

As used herein the phrase "whitening efficacy" is intended to refer to the amount of change in tooth color. The color change can be measured according to the LAB color scale. FIG. 4 illustrates a model of the 1976 CIE LAB color space. The luminance or lightness (L*) value measures brightness and varies from a value of one hundred for perfect white to zero for black assuming a* and b* are zero. The a* value is a measure of redness when positive, gray when zero and greenness when negative. The b* value is a measure of yellowness when positive, gray when zero and blueness when negative. Generally, teeth appear whiter as: the L value increases meaning they become brighter, the a* value increases or decreases depending upon whether the stained teeth have a green or red tint prior to whitening, and the b* value decreases meaning they become less yellow. While this is the general relationship for perceived whitening, the b* value might also slightly increase if the magnitude of the increase of the L* value is large enough. Similarly, the L* value might also decrease if the magnitude of the decrease of the b* value is large enough to overshadow the less significant change in L*. Because the color of actual stained teeth varies by different geographies, whether the a* value increases or decreases for whitening can be geography dependent. For instance, stained teeth have a brown or red tint in the United States while stained teeth have a green tint in China.

A method of measuring tooth color change in-vivo has been described in U.S. Pat. No. 6,949,240 and ASTM E2466-06, the entire disclosures of which have been incorporated herein by reference. In such a method, a digital camera is used to compare baseline and post-whitening tooth color to RGB color standards imaged to establish calibration set-points. The RGB values are transformed into L*a*b* values after calibration using transformation equations, and the resulting data is used to calculate product whitening performance in terms of changes in L* (luminance), a* (red-green balance), and b* (yellow-blue balance). An overall color change is calculated using the equation $\Delta E=(\Delta L^{*2}+\Delta a^{*2}+\Delta b^{*2})^{1/2}$.

When $\Delta L^*$ is positive, $\Delta b^*$ is negative and a* is moving towards zero, $\Delta E$ represents an improvement in tooth whiteness. $\Delta E$ is a scalar value, and therefore it represents the magnitude of the color change, but not the direction. For that reason, the direction of the changes in the indiviual color components L*, a* and b* must be evaluated to determine whether the $\Delta E$ value represents an improvement in tooth whiteness.

Light radiation has been employed in tooth whitening procedures in combination with the application of an oxidizing agent to the teeth. However, the previous use of light radiation in tooth whitening procedures, while increasing tooth whitening efficacy, may produce increased tooth and soft tissue sensitivity and discomfort, or other harmful effects. As one example, U.S. Pat. No. 4,661,070 describes a method in which a concentrated solution of hydrogen peroxide is applied to the teeth, which are then exposed to infrared and ultraviolet light. The infrared light radiation is intended to produce heat to penetrate the outer tooth surface and heat activate the peroxide, while the ultraviolet light is intended to provide direct bleaching of the tooth stains. However, excessive temperature increases in the pulpal tissue may damage teeth and cause sensitivity and discomfort. Further, health hazards associated with exposure to ultraviolet light are also a concern.

Tooth whitening using photoactivation of a radiant energy absorbing substance or photosensitizing agent (for example, 1-hydroxyethylidene-1,1-diphosphonic acid) applied to a dental patient's teeth has been described for example in U.S. Pat. Nos. 5,785,527, 6,162,055, and 6,416,319, the entire disclosures of which are incorporated herein by reference. In such examples, the photosensitizing agent may be applied prior to or in combination with an oxidizing agent (for example, hydrogen peroxide), such that light radiation applied to the treated teeth is absorbed by the photosensitizing agent, which in turn activates the oxidizing compound to whiten the teeth. However, inadvertent exposure of a user's soft tissue to the photosensitizing agent may result in irritation and increased sensitivity upon application of the light radiation.

Clinical testing of light radiation enhancement of in-office, high concentration peroxide gel tooth whitening treatments has identified measurable increases in whitening efficacy, as compared to peroxide gel tooth whitening treatments alone. See Gerald Kugel et al., *Clinical Trial Assessing Light Enhancement of In-office Tooth Whitening*, JOURNAL OF ESTHETIC AND RESTORATIVE DENTISTRY, Oct. 1, 2009, pp. 336-346, the entire disclosure of which is incorporated herein by reference. However, these increases in tooth whitening efficacy were accompanied by significant increases in tooth sensitivity. In the clinical test, six of the eleven test subjects treated with peroxide gel and light radiation reported moderate to severe tooth pain, with three of the test subjects discontinuing treatment due to severe tooth pain. By comparison, only three of the eleven test subjects treated with peroxide gel without light radiation reported moderate pain, with none of these test subjects experiencing severe pain. It is not known whether a photosensitizing agent was included in the peroxide gel that was used, nor is it known whether such use of a photosensitizing agent in the peroxide gel, combined with the prolonged light treatment, may have contributed to the significant increase in tooth sensitivity.

In other examples, a light radiation may be selected to activate the tooth stains directly, without the use of a photosensitizing agent, to enhance bleaching by an oxidizing compound. Light having a wavelength selected to correspond with a tooth chromogen (or stain) molecule absorption wavelength may be applied to the teeth to activate the stain molecules for oxidation by the oxidizing compound. In such an example, the light radiation may not activate or affect the oxidizing compound. The oxidizing compound may be provided as a transparent or translucent material to allow the light radiation to reach the treated teeth. Absorption of the light radiation by the stain "activates" the stain by promoting electron activity or reactivity, such that a bleaching agent applied to the stain more effectively oxidizes the stain, thereby removing a greater portion of the stain, as compared to oxidation by a bleaching agent of a stain that has not been activated by this light radiation.

Even without a photosensitizing agent, exposure of the gums and other soft tissue to the light radiation may cause some activation of this tissue. This may result in increased sensitivity and irritation when the same tissue is exposed to higher concentrations of peroxide or some other oxidizing agent.

According to an inventive aspect of the present application, application of light radiation to teeth treated with a tooth whitening composition having an oxidizing agent may be limited to a delayed or final portion of the total duration of exposure of the teeth to the tooth whitening composition. By limiting the light radiation to just a portion of the entire duration of the treatment, irritation and sensitivity of the teeth and soft tissue exposed to the oxidizing agent may be reduced. Additionally, temperature increases within the user's mouth may also be reduced. Further, by limiting light radiation to a final portion of the entire duration of treatment, the application of light is provided during a period at which absorption of the oxidizing agent into the teeth is maximized, and dissipation of the oxidizing agent away from the soft tissue (for example, by dissolution into the user's saliva) has occurred. As still another benefit, the application of light radiation for a reduced period of time reduces the duration of an open mouth or retracted lip condition, thereby reducing the soreness and oral dehydration associated with these conditions.

Accordingly, a predetermined duration of tooth whitening treatment is divided into two time periods: a delay or first time period and a light radiation or second time period. During the delay period, a chemical whitening composition is maintained on a user's teeth without the application of light radiation. During a subsequent second time period (the light radiation period), light radiation is applied to the teeth. The light radiation may be applied through a translucent chemical whitening composition (and any corresponding translucent carrier for the composition, such as a tray or adhesive strip). In another embodiment, the tooth whitening composition (and any corresponding carrier) may be removed from the teeth after the delay period and before the light radiation period, as described in greater detail below, or during the light radiation period. In one embodiment, the delay period is greater than the light radiation period, or greater than 50% of a total duration of the delay and light radiation periods, such that the teeth are exposed to light radiation for less than half of the entire duration of the tooth whitening treatment. The delay period may also be greater than about 60%, greater than about 70%, greater than about 80%, greater than about 90%, greater than about 95%, or greater than about 96%, or greater than about 97%, or greater than about 98%, or greater than about 99%, or greater than about 99.5%, or greater than about 99.9%, or between about 80% and about 90% of the total duration of the delay and light radiation periods.

The delay period, light radiation period, and total duration of the delay and light radiation periods may be selected from a variety of suitable numbers and ranges. For example, the delay period may range from about 2 minutes to about 480 minutes, or from about 5 minutes to about 55 minutes, or from about 15 minutes to about 25 minutes. In another embodiment, the delay period may be at least 1, 2, 5, 7, 10, 15, 20, 25, 30, 40, 50, or 60 minutes, but less than 480, 120, 90, 60, 50, 40, 30, 25, 20, 15, 10, 5, or 2 minutes.

The light radiation period may range for example from about 3 seconds to about 30 minutes, or from about 30 seconds to about 10 minutes, or from about 2 minutes to about 5 minutes. In another embodiment, the light radiation period may be at least 1, 2, 5, 7, 10, 15, 20, 25, 30, 40, 50, or 60 seconds, 2, 3, 4, minutes but less than 5, 4, 3, 2, or 1 minutes, 50, 40, 30, 25, 20, 15, 10, or 5 seconds.

The total duration of the delay and light radiation periods may range for example from about 4 minutes to about 500 minutes, or from about 10 minutes to about 60 minutes, or from about 15 minutes to about 30 minutes. In another embodiment, the total duration may be at least 4, 5, 7, 10, 15, 20, 25, 30, 40, 50, 60, 90, 120, 180, or 240 minutes, but less than 500, 480, 420, 360, 300, 240, 80, 120, 90, 60, 50, 40, 30, 20, or 15 minutes. In some applications, a tooth whitening composition and carrier may be designed for overnight use, such that a relatively long delay period (for example, between about 360 minutes and about 480 minutes) occurs while the user is sleeping.

Thus, in varying embodiments, the total duration may be at least 4, 5, 7, 10, 15, 20, 25, 30, 40, 50, 60, 90, 120, 180, or 240 minutes, but less than 500, 480, 420, 360, 300, 240, 80, 120, 90, 60, 50, 40, 30, 20, or 15 minutes; combined with a light radiation period of at least 1, 2, 5, 7, 10, 15, 20, 25, 30, 40, 50, or 60 seconds, 2, 3, 4, minutes but less than 5, 4, 3, 2, or 1 minutes, 50, 40, 30, 25, 20, 15, 10, or 5 seconds; further combined with a delay period of at least 1, 2, 5, 7, 10, 15, 20, 25, 30, 40, 50, or 60 minutes, but less than 480, 120, 90, 60, 50, 40, 30, 25, 20, 15, 10, 5, or 2 minutes.

Additionally, the tooth whitening process may include a third time period or second delay period after the light radiation period, during which the tooth whitening composition remains on the teeth without light treatment prior to removal. This second delay period may range for example from about 1 minute to about 30 minutes.

In one exemplary tooth whitening method, an approximately thirty minute tooth whitening treatment includes an approximately twenty-five minute delay period and an approximately five minute light radiation period. In another exemplary tooth whitening method, an approximately thirty minute tooth whitening treatment includes an approximately twenty-nine and one-half minute delay period and a light radiation period of approximately 30 seconds.

Other exemplary tooth whitening regimens are listed in Table 1 below:

TABLE 1

Exemplary Delay and Light Radiation Periods for Tooth Whitening Treatments

| Delay Period (mins) | Light Period (mins) | Total (mins) | % Delay Period |
|---|---|---|---|
| 2 | 2 | 4 | 50.00 |
| 4 | 2 | 6 | 66.67 |
| 10 | 3 | 13 | 76.92 |
| 10 | 0.5 | 10.5 | 95.24 |
| 15 | 3 | 18 | 83.33 |
| 15 | 0.5 | 15.5 | 96.77 |
| 15 | 5 | 20 | 75.00 |
| 20 | 0.5 | 20.5 | 97.56 |
| 20 | 1 | 21 | 95.24 |
| 20 | 3 | 23 | 86.96 |
| 20 | 5 | 25 | 80.00 |
| 25 | 0.05 | 25.05 | 99.80 |
| 25 | 0.5 | 25.5 | 98.04 |
| 25 | 1 | 26 | 96.15 |
| 25 | 3 | 28 | 89.29 |
| 25 | 5 | 30 | 83.33 |
| 25 | 10 | 35 | 71.43 |
| 30 | 0.05 | 30.05 | 99.83 |
| 30 | 0.5 | 30.5 | 98.36 |
| 30 | 1 | 31 | 96.77 |
| 30 | 3 | 33 | 90.91 |
| 30 | 5 | 35 | 85.71 |
| 30 | 10 | 40 | 75.00 |
| 60 | 0.05 | 60.05 | 99.92 |
| 60 | 0.5 | 60.5 | 99.17 |
| 60 | 5 | 65 | 92.31 |
| 120 | 0.5 | 120.5 | 99.59 |
| 120 | 5 | 125 | 96.00 |
| 120 | 10 | 130 | 92.31 |
| 120 | 60 | 180 | 66.67 |
| 360 | 0.5 | 360.5 | 99.86 |
| 360 | 5 | 365 | 98.63 |
| 360 | 10 | 370 | 97.30 |
| 480 | 0.5 | 480.5 | 99.90 |
| 480 | 5 | 485 | 98.97 |
| 480 | 10 | 490 | 97.96 |
| 480 | 20 | 500 | 96.00 |

The durations of the delay and light radiation periods of the tooth whitening treatment may be selected based on several factors. For example, the delay period may be selected to allow the oxidizing or bleaching agent sufficient time to reach the tooth stains below the outer surfaces of the teeth before light activation of the stains. In one such embodiment, a delay period sufficient for absorption of an effective amount of peroxide into the teeth is selected for delaying the application of light radiation until a period of increased effectiveness. Because the applied light radiation activates the tooth stains directly, as enhanced by the absorbed oxidizing agent, the residual tooth whitening composition on the surface of the teeth (and any tooth whitening composition carrier) may be removed from the teeth at the end of the delay period and prior to the application of light radiation. In one such tooth whitening process, the carrier and/or the tooth whitening composition may be provided in a non-transparent, non-translucent, or opaque material, as the carrier and/or tooth whitening composition will have been removed prior to light treatment. The ability to use non-transparent, non-translucent, or opaque materials may increase the number of types of materials that may be used for the carrier and tooth whitening composition. Additionally, in some applications, the use of non-transparent, non-translucent, or opaque materials for the tooth whitening composition or carrier may prevent the irritation or sensitivity that may otherwise result from a combination of light radiation and excessive amounts of tooth whitening composition on the teeth and soft tissues.

As another example, the delay period may be selected to allow bleaching agent on the soft tissue surrounding the treated teeth to dissipate or be diluted (for example, by saliva) prior to any application of light radiation. This may reduce any soft tissue irritation that may otherwise result from a combination of light radiation and bleaching agent on the soft tissue. In one such embodiment, a time period sufficient to reduce a peroxide concentration at the soft tissue to below a threshold concentration is selected for delaying the application of light radiation until a period of reduced susceptibility to soft tissue irritation. For example, the selected time period may be sufficient to reduce a peroxide (or other bleaching agent) concentration to less than about 2% (weight for weight), less than about 1%, less than about 0.5%, less than about 0.25%, less than about 0.1%, less than about 0.05%, less than about 0.025%, less than about 0.0125% or less than about 0.005%.

The duration of the light radiation period of the tooth whitening treatment may be selected to increase whitening efficacy while minimizing tooth and soft tissue sensitivity. Clinical testing, as described in Example I below, has shown greater increases in luminance ($\Delta L^*$) and yellowness reduction ($\Delta b^*$), as compared to treatment without light enhancement, as the light radiation period is increased at the conclusion of treatment. One of ordinary skill in the art will recognize that additional testing may be performed using a greater range of delay periods and light radiation periods in conjunction with any suitable tooth whitening composition, to determine an appropriate delay period of a total time period and an appropriate light radiation period of the total time period, to provide increased whitening efficacy while minimizing tooth and soft tissue sensitivity, in accordance with the present application.

While a minimum light intensity may be required to activate tooth stains for enhanced whitening, according to an aspect of the present application, variations in light intensity above a required threshold may have minimal impact on whitening efficacy. Clinical testing, as described in Example II below, has shown that while light intensities as low as approximately 41.5 mW/cm$^2$ (corresponding to light emitted from a Lite-ON Technology Corp. LED part # LTL1CHTBK5 BIN: QBOY 470 nm supplied with about 10 mA of current) resulted in significant improvements in increased luminance and reduced yellowness (as compared to treatment without light enhancement), increasing light intensity to as much as approximately 134.7 mW/cm$^2$ (corresponding to light emitted from the above referenced Lite-ON Technology Corp. LED supplied with about 50 mA of current) resulted in only marginal improvements in whitening efficacy. This suggests that low intensity (at least as low as about 41.5 mW/cm$^2$) light is sufficient to activate the tooth stains to an elevated quantum energy level, while the increased intensity (at least as high as about 134.7 mW/cm$^2$) light is insufficient to elevate the tooth stains to the next quantum energy level for greater activation.

The effectiveness of low intensity light radiation treatment may facilitate home use of the light enhanced tooth whitening process, as self-application of the low intensity light radiation would likely be safe for adult use. For example, low intensity light radiation is less likely to result in increased temperatures at the teeth or in the mouth, and is less likely to cause oral dehydration. The use of low intensity light also reduces the risk of damage to the eyes. In-home application of a low-intensity light enhanced tooth whitening treatment may be further facilitated by use of a tooth whitening composition and carrier that provides for controlled dosing of a bleaching agent without requiring isolation of the surrounding soft tissue. Examples of suitable tooth whitening products include the strip-based tooth whitening products described in the incorporated U.S. Pat. No. 6,949,240.

Figure 2:
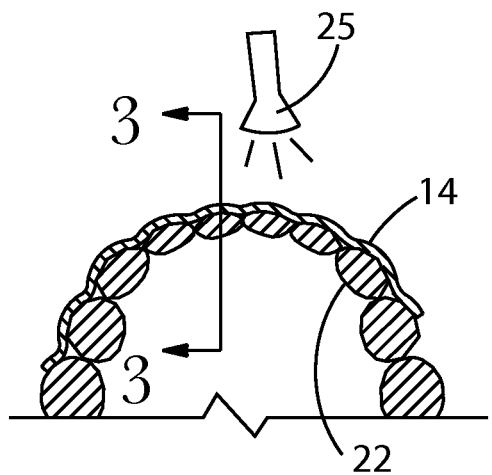
FIG. 2 is a cross-sectional plan view of human dentition, illustrating application of the light enhanced tooth whitening kit of FIG. 1 for treatment of a front surface of a plurality of teeth.
Figure 3:
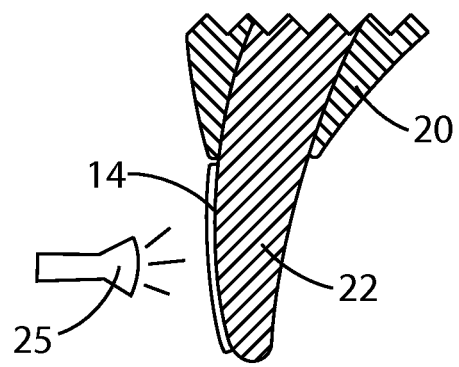
FIG. 3 is a cross-sectional side elevation view of a tooth of FIG. 2, taken along line 3-3 thereof.

Accordingly, a light enhanced tooth whitening kit 10 for home use may be provided, as shown in FIGS. 1-3. The kit 10 may include a translucent strip 14 sized to cover one or more teeth 22, with the strip including a layer 12 of a translucent tooth whitening composition disposed on a surface 28 of the strip 14. The kit 10 further includes a portable light source 25 (for example, a flashlight) configured to emit light radiation having a maximum energy output of about 10,000 millicandelas (mcd) or a maximum intensity of about 150 mW/cm$^2$, or some other maximum energy output or intensity that is safe for use near the eyes yet sufficient to activate the tooth stains. The portable light source may be held against the tooth whitening composition carrier or directly against the teeth (for example, if the carrier has been removed prior to light radiation treatment). The portable light source may also be held at a suitable distance from the teeth, such as for example between about 0.5 cm and about 3 cm or approximately 2 cm. The resulting light intensity to which the teeth are exposed will depend on the distance of the light source from the teeth and the energy output of the light source. Exemplary ranges of light intensity at the teeth during the light radiation period of a light enhanced tooth whitening process include for example between about 0.05 mW/cm$^2$ and about 200 mW/cm$^2$, between about 0.1 mW/cm$^2$ and about 180 mW/cm$^2$, between about 1 mW/cm$^2$ and about 160 mW/cm$^2$, between about 5 mW/cm$^2$ and about 140 mW/cm$^2$, between about 10 mW/cm$^2$ and about 120 mW/cm$^2$, between about 20 mW/cm$^2$ and about 100 mW/cm$^2$, between about 30 mW/cm$^2$ and about 80 mW/cm$^2$, and between about 40 mW/cm$^2$ and about 60 mW/cm$^2$. In other examples, light intensity at the teeth during the light radiation period of a light enhanced tooth whitening process may be between about 40 mW/cm$^2$ and about 140 mW/cm$^2$, or approximately 42 mW/cm$^2$, or approximately 108 mW/cm$^2$, or approximately 135 mW/cm$^2$.

The portable light source may optionally include a timer for indicating starting or stopping points for the delay period and/or the light radiation period, and may be configured to limit the emission of light radiation to the latter period. In another embodiment, a tooth whitening composition carrier may be provided with a portable light source (for example, one or more LED chips) disposed on or in the carrier, such that light may be directed onto the teeth by the carrier. In one such example, the carrier may further include a timer circuit that delays illumination of the portable light source for a predetermined delay period, and then illuminates the teeth for a predetermined light radiation period.

The light source 25 utilized for the light enhanced tooth whitening treatment may be selected to provide light radiation at a wavelength that is best absorbed by the tooth stains. The light radiation may be selected to be at a wavelength corresponding to a light color diametrically opposite the stain color, as identified for example on the 1976 CIE LAB color scale (see FIG. 4). By utilizing a diametrically opposite light color, absorption of the light by the stain may be increased or enhanced. For example, yellow stains (as commonly present on teeth to be whitened) may better absorb blue light (approximately 380-520 nm). As such, the light source may be selected to provide light radiation at a wavelength of about 400 nm to about 520 nm, or about 440 nm to about 490 nm, or an average wavelength of approximately 440 nm, or approximately 450 nm, or approximately 460 nm, or approximately 470 nm, or approximately 480 nm, or approximately 490 nm. As another example, green stains may better absorb red light, such as for example light having a wavelength of about 600 nm to about 780 nm. As such, a light source for use in whitening green stains may be selected to provide light radiation at a wavelength of about 600 nm to about 780 nm, or about 680 nm to about 720 nm, or an average wavelength of approximately 680 nm, or approximately 690 nm, or approximately 700 nm, or approximately 710 nm, or approximately 720 nm.

Additionally or alternatively, the tooth whitening composition or carrier (for example, a tray or strip) may be configured to shade, filter, or otherwise block undesirable light intensities and wavelengths, thereby adapting the light radiation from the light source that reaches the tooth stain to be within desired ranges of intensity and wavelength. For example, a tooth whitening composition carrier may be provided in a translucent material selected to block up to about 30% of light, or up to about 50% of light, or up to about 70% of light. As another example, a tooth whitening composition carrier may be provided in a translucent material selected to block light having a wavelength greater than about 780 nm, or greater than about 700 nm, or greater than about 520 nm, or less than about 300 nm, or less than about 380 nm.

Many different tooth whitening compositions and application methods may be utilized in combination with the light radiation treatment described above. For example, peroxide based tooth whitening compositions with varying concentrations of peroxide may be provided. Other additives may also be provided in the composition, including for example photosensitizing agents, gelling agents, humectants, pH adjusting agents, stabilizing agents, desensitizing agents, and accelerating agents or bleach activators. The composition may be provided in the form of a viscous liquid, paste, gel, solution, or any other state or phase that may be applied to the teeth. Further, the tooth whitening composition may be applied directly to the teeth, or may be contained by a tray placed over the teeth or provided on a strip of flexible material configured to be applied to the tooth surfaces to be whitened. Examples of such tooth whitening compositions and application methods are described in U.S. Pat. No. 6,949,240, and U.S. Application Publication No. 2003/0152528, the entire disclosures of which are incorporated herein by reference.

Figure 5:
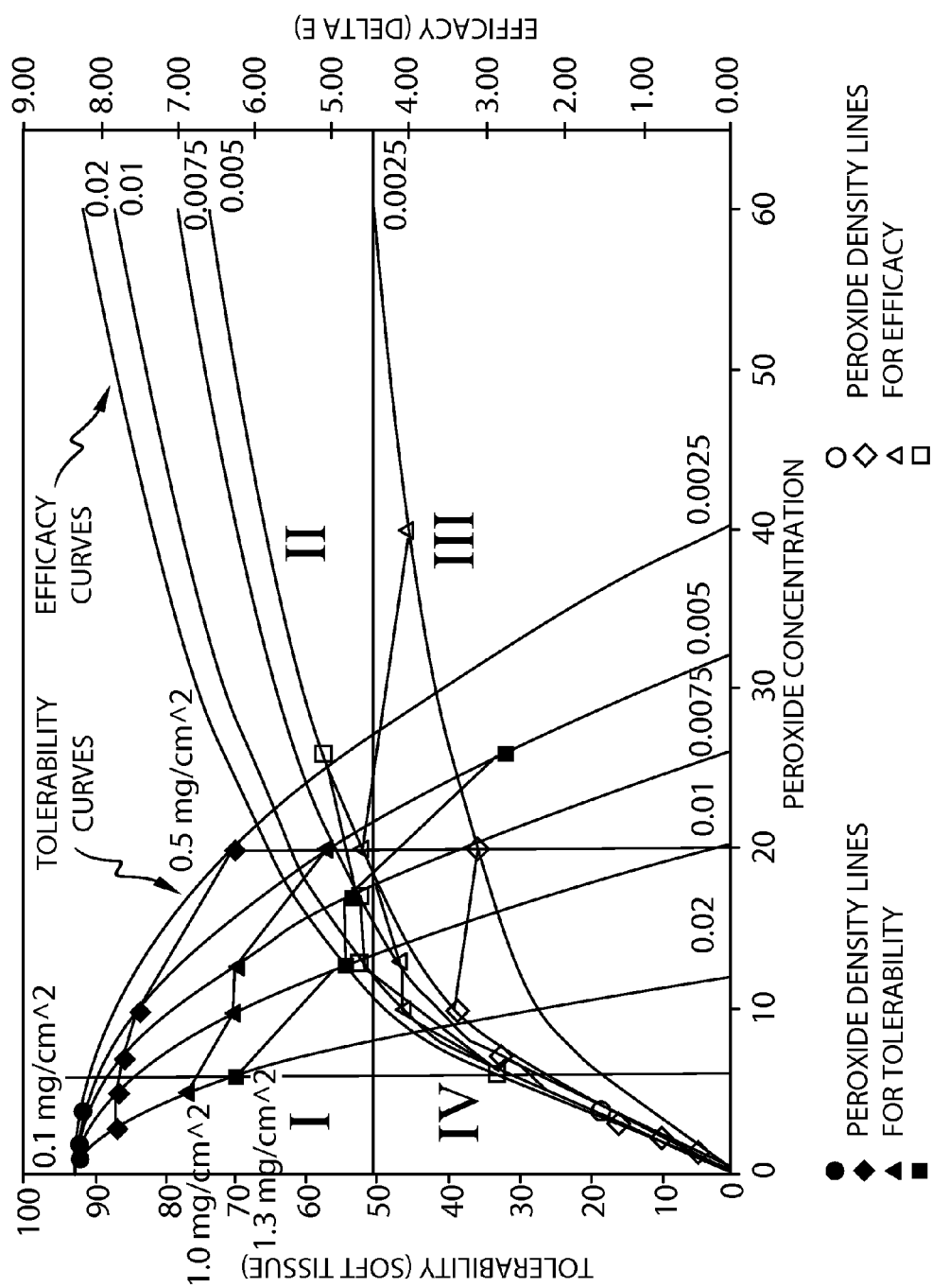
FIG. 5 is a graph illustrating the interplay between whitening efficacy, soft tissue tolerability, peroxide concentration, composition loading and peroxide dosing, according to a non-light enhanced tooth whitening method.

Several factors may be considered in selecting an appropriate whitening composition and application method, including for example whitening efficacy, soft tissue tolerability, peroxide concentration, and whitening composition loading. Generally, in non-light enhanced tooth whitening applications, as peroxide concentration increases, whitening efficacy increases as shown by the upward slope of the efficacy curves of the graph of FIG. 5, described in greater detail in U.S. Pat. No. 6,949,240. Additionally, soft tissue tolerability decreases as peroxide concentration increases, as shown by the downward slope of the tolerability curves of the graph of FIG. 5. From this family of curves, it will be appreciated that it is possible to maintain acceptable soft tissue tolerability while increasing whitening efficacy by increasing the peroxide concentration to relatively high levels if there is an appropriate decrease in composition loading. Stated another way, it is possible to increase the concentration of the peroxide active to achieve improved whitening efficacy while maintaining acceptable soft tissue tolerability, without the use of artificial barriers, by properly selecting the composition loading. This relationship can also be characterized by a parameter, peroxide density, which is the ratio of the amount of peroxide active or peroxide dose (mg) to the surface area (cm$^2$) of the thin layer that is applied to the tooth surfaces and adjacent soft tissue of the oral cavity. This surface area may be different than the "exposed surface area" and/or "unexposed surface area," as discussed in U.S. Pat. No. 6,949,240.

In one embodiment of U.S. Pat. No. 6,949,240, so long as the peroxide density is less than about 1.3 mg peroxide/cm$^2$, there can be an acceptable tradeoff between soft tissue tolerability and whitening efficacy for peroxide concentrations greater than at least about 7.5%. While extremely high peroxide concentrations can be surprisingly utilized, generally it is desirable to utilize peroxide concentrations less than 60% and, even more desirable to have a peroxide density less than about 1.3 mg/cm$^2$ for tooth whitening applications, because the soft tissue tolerability is acceptable to very good. This controlled peroxide density may likewise limit tooth and soft tissue sensitivity in light enhanced peroxide treatments, as described herein.

In other embodiments, the peroxide density is less than about 1.2 mg/cm$^2$, or less than about 1.1 mg/cm$^2$, or less than about 1 mg/cm$^2$, or less than about 0.75 mg/cm$^2$, or less than about 0.5 mg/cm$^2$, and/or greater than about 0.01 mg/cm$^2$, or greater than about 0.1 mg/cm$^2$, or greater than about 0.25 mg/cm$^2$, or greater than about 0.5 mg/cm$^2$ in combination with a peroxide concentration greater than about 7.5%, or greater than about 8%, or greater than about 10%, or greater than about 12%, or greater than about 16%, or greater than about 20%, and/or less than about 40%, or less than about 35%, or less than about 30%, or less than about 20%. The peroxide active can be any form that liberates peroxide either by solubilization or hydration. All peroxide active concentrations expressed herein are for hydrogen peroxide and appropriate conversions must be made for other peroxide liberating molecules such as carbamide peroxide, calcium peroxide and sodium percarbonate, etc. Some other peroxide actives suitable for use with the present invention include calcium peroxide, carbamide peroxide, sodium percarbonate, benzoyl peroxide and mixtures thereof. A method for determining the concentration of the peroxide active is set forth in the incorporated disclosure of U.S. Pat. No. 6,949,240.

The total amount of the tooth whitening composition that is delivered to the oral cavity will vary depending upon the size of the strip of material 12 and the concentration of the peroxide active. Generally, greater than about 0.0002 gram of tooth whitening composition is provided with the present invention, or greater than about 0.005 gm, or greater than about 0.01 gm, or greater than about 0.015 gm, or greater than about 0.02 gm, or greater than about 0.025 gm, or greater than about 0.05 gm, or greater than about 0.075 gm, or greater than about 0.1 gm, or greater than about 0.15 gm, or greater than about 0.2 gm and/or less than about 0.3 gm, or less than about 0.2 gm, or less than about 0.15 gm, or less than about 0.1 gm, or less than about 0.05 gm, or less than about 0.025 gm, or less than about 0.001 gm.

The tooth whitening composition loading may be greater than about 0.0005 gm/cm$^2$, or greater than about 0.001 gm/cm$^2$, or greater than about 0.002 gm/cm$^2$, or greater than about 0.0025 gm/cm$^2$, or greater than about 0.005 gm/cm$^2$, or greater than about 0.0075 gm/cm$^2$, or greater than about 0.01 gm/cm$^2$, or greater than about 0.015 gm/cm$^2$, and/or less than about 0.03 gm/cm$^2$, or less than about 0.02 gm/cm$^2$, or less than about 0.015 gm/cm$^2$, or less than about 0.01 gm/cm$^2$, or less than about 0.005 gm/cm$^2$, or less than about 0.001 gm/cm$^2$.

As previously discussed, the tooth whitening composition contains a peroxide active and is provided in a thin layer 12 on a strip of material 14. In order to achieve the previously described composition loadings at the higher peroxide concentrations, the thin layer 12 of tooth whitening composition that is applied to the oral cavity may have a thickness less than about 0.3 mm, or less than about 0.2 mm, or less than about 0.15 mm, or less than about 0.1 mm, or less than about 0.06 mm, or less than about 0.03 mm, or less than about 0.001 mm and/or greater than about 0.0002 mm, or greater than about 0.004 mm, or greater than about 0.008 mm, or greater than about 0.016 mm, or greater than about 0.018 mm, or greater than about 0.02 mm, or greater than about 0.1 mm, or greater than about 0.15 mm. These measurements are taken by measuring from the surface 28 (FIG. 1) of the strip of material 14 and up through the thin layer 12 of tooth whitening composition.

The peroxide dose, which is the total amount of the peroxide active within the thin layer of the tooth whitening composition that is applied to the oral cavity, is less than about 100 mg, or less than about 95 mg, or less than about 85 mg, or less than about 80 mg, or less than about 40 mg, or less than about 20 mg, or less than about 15 mg, or less than about 12 mg, or less than about 10 mg, or less than about 5 mg, or less than about 1 mg, and/or greater than about 0.1 mg, or greater than about 0.3 mg, or greater than about 0.6 mg, or greater than about 1 mg, or greater than about 1.5 mg, or greater than about 2 mg, or greater than about 10 mg.

While it is desirable for the thin layer 12 of the tooth whitening composition to be a homogeneous, uniform and continuous layer, the thin layer 12 may also be non-uniform, non-continuous, and/or heterogeneous. For example, the thin layer 12 can be a laminate or separated layers of components, an amorphous mixture of components, separate stripes or spots or other patterns of different components, or a combination of these structures.

The tooth whitening composition of the present invention can be provided in the form of a viscous liquid, paste, gel, solution, or any other suitable state or phase. The tooth whitening composition can be provided in the form of a gel with a viscosity between about 200 and about 1,000,000 cps at low shear rates (approximately one seconds$^{-1}$). In another embodiment, the viscosity is between about 100,000 and about 800,000 cps or between about 150,000 and about 700,000 cps. In yet another embodiment, the viscosity is between about 300,000 and about 700,000 cps.

As known in the art, the tooth whitening composition also has a yield stress. Yield stress is the amount of force on a material before the material begins to move. The yield stress must be high enough so that the tooth whitening composition is able to form a thin layer and also to handle the disturbances caused by manufacturing, handling, and storage. The yield stress of the tooth whitening composition is between about 2 Pascals and about 3000 Pascals, preferably between about 20 Pascals and about 2000 Pascals, more preferably between about 200 Pascals and about 1500 Pascals, and most preferably between about 200 Pascals and about 400 Pascals.

Additional constituents of the tooth whitening composition can include, but are not limited to, water, gelling agents, humectants, pH adjusting agents, stabilizing agents, desensitizing agents, and accelerating agents or bleach activators. In addition to the above materials, a number of other materials can also be added to the substance. Additional materials include, but are not limited to, flavoring agents, sweetening agents such as saccharin, xylitol, opacifiers, coloring agents, and chelants such as ethylenediaminetetraacetic acid. These additional ingredients can also be used in place of the compounds disclosed above. Use of these additives and additional materials is described in greater detail in the incorporated disclosure of U.S. Pat. No. 6,949,240.

EXAMPLE I

A randomized, parallel, split-mouth design clinical trial is conducted on thirty-five adults with a Vita Shade tooth color of A2+ who had not undergone tooth bleaching treatments in the previous two years and had no tooth sensitivity. The subjects are randomly assigned to one of six sequences that designate which side of the mouth and treatment they receive. Each subject uses a 10% hydrogen peroxide marketed whitening strip (CREST WHITESTRIPS PREMIUM) on their maxillary teeth for 30 minutes once a day for seven days. One of the lateral incisors is treated with an LED light source (Lite-ON Technology Corporation, 720 South Hillview Drive, Milpitas, Calif. 95035, part # LTL1CHTBK5 BIN: QBOY 470 nm) having an intensity of about 134.7 mW/cm$^2$ (resulting from a current of about 50 mA supplied to the LED) and an average wavelength of 468 nm for 3, 30 or 300 seconds at the end of the 30 minute strip wear time according to the randomization schedule. The other lateral incisor is treated without light enhancement to establish a control measurement. Digital images are collected at initial screening, on the fourth day of the treatment ("Day 4"), and the day after completion of the treatment ("Day 8").

Treatment groups are balanced with respect to the demographics and baseline (pre-treatment) tooth color. Each treatment (including "strip only" control treatments) results in significant (p<0.02) reduction of b* and L* color parameters relative to baseline at each study visit. The 300 second light treatment results in significantly greater yellowness reduction ($\Delta$b*), increased luminance ($\Delta$b*), and resultant color change (ΔE) relative to the corresponding control measurement, as shown in Table 2 below, with 97% greater luminance increase and 69% greater yellowness reduction at Day 8.

TABLE 2

Day 8 Tooth Whitening Efficacy with Five Minute Light Radiation Treatment

| Treatment | Delta L* | Delta a* | Delta b* | Delta E* |
|---|---|---|---|---|
| Light | 1.68 | −0.54 | −1.81 | 2.54 |
| No Light | 0.85 | −0.47 | −1.07 | 1.72 |
| % Difference | 97% | 15% | 69% | 48% |
| p-value | 0.047 | 0.46 | 0.002 | 0.031 |

The 30 second light treatment also results in significantly greater yellowness reduction relative to the corresponding control measurement, with 27% greater yellowness reduction at Day 8. All treatments are well-tolerated, with no subjects discontinuing treatment because of tooth pain or oral irritation.

End-of-treatment (Day 8) results for Δb* for all three treatment times are shown in Table 3 below:

TABLE 3

Day 8 Yellowness Reduction with Varying Light Radiation Times

| Treatment | Adjusted mean change from Baseline | Change from Control based on adjusted means |
|---|---|---|
| 3 sec light + strip | −0.89 | 0.22 |
| 30 sec light + strip | −1.50 | −0.28 |
| 300 sec light + strip | −1.66 | −0.82 |

Figure 6:
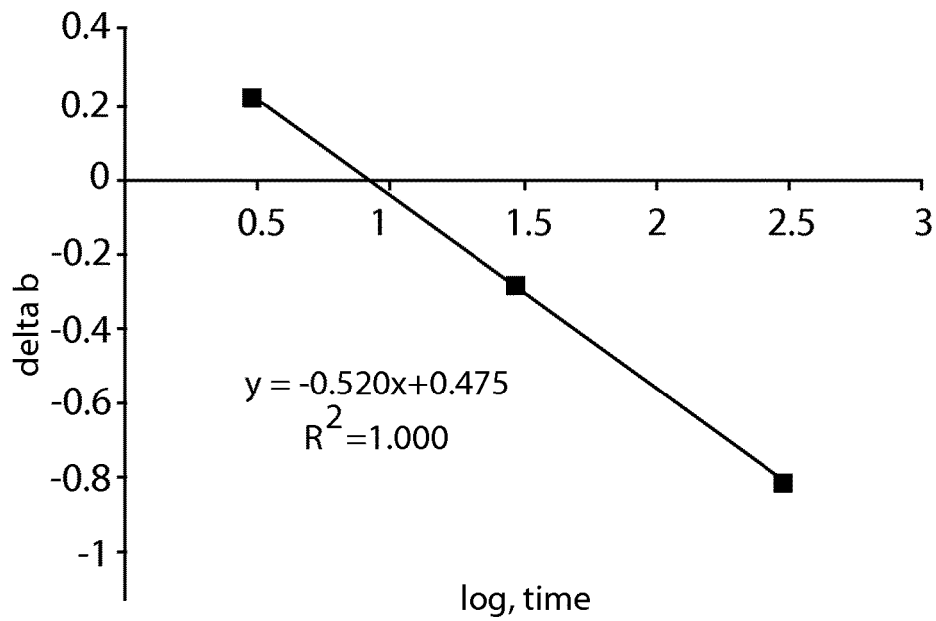
FIG. 6 is a graph illustrating the interplay between duration of light radiation treatment and tooth whitening efficacy.

The relationship between exposure time and Δb* change from control based on adjusted means is illustrated in the graph shown in FIG. 6.

EXAMPLE II

A randomized, parallel, split-mouth design clinical trial is conducted on thirty-five adults with a Vita Shade tooth color of A2+ who had not undergone tooth bleaching treatments in the previous two years and had no tooth sensitivity. The subjects are randomly assigned to one of six sequences that designate which side of the mouth and treatment they receive. Each subject used a 10% hydrogen peroxide marketed whitening strip (CREST WHITESTRIPS PREMIUM) on their maxillary teeth for 30 minutes once a day for ten days. One of the lateral incisors is treated with light radiation having an average wavelength of 468 nm and an intensity of approximately 41.5 mW/cm$^2$, approximately 108 mW/cm$^2$, or approximately 134.7 mW/cm$^2$ (corresponding to light emitted from the LTL1CHTBK5 BIN: QBOY 470 nm LED, described above, when in contact with the whitening strip and supplied with about 10 mA, 25 mA, and 50 mA of current, respectively) for five minutes at the end of the 30 minute strip wear time. The other lateral incisor is treated without light enhancement to establish a control measurement. Digital images are collected at initial screen, on the fourth day of the treatment ("Day 4"), on the eighth day of the treatment ("Day 8"), and the day after completion of the treatment ("Day 11").

Treatment groups are balanced with respect to the demographics and baseline (pre-treatment) tooth color. Each treatment (including "strip only" control treatments) results in significant (p<0.04) reduction of yellowness (b*) as early as Day 4 and increased lightness (L*) at Day 11 of the study. All light enhanced peroxide strip treatments demonstrate significantly (p<0.0001) greater yellowness reduction (Δb*) relative to their corresponding controls at each study visit. The ΔL* parameters are not significantly different between the treatment groups. No significant differences are observed between the 41.5 mW/cm$^2$, 108 mW/cm$^2$, and 134.7 mW/cm$^2$ light treatments. All treatments are well-tolerated, with only two of the thirty-five total subjects reporting tooth sensitivity and two of the total subjects reporting oral irritation.

End-of-treatment (Day 11) results for Δb* are shown in Table 4 below:

TABLE 4

Day 11 Yellowness Reduction with Varying Light Radiation Intensity

| Treatment | Adjusted mean change from Baseline | Change from Control based on adjusted means |
|---|---|---|
| 10 mA light + strip | −1.96 | −1.07 |
| 25 mA light + strip | −2.55 | −1.11 |
| 50 mA light + strip | −2.41 | −1.19 |

Figure 7:
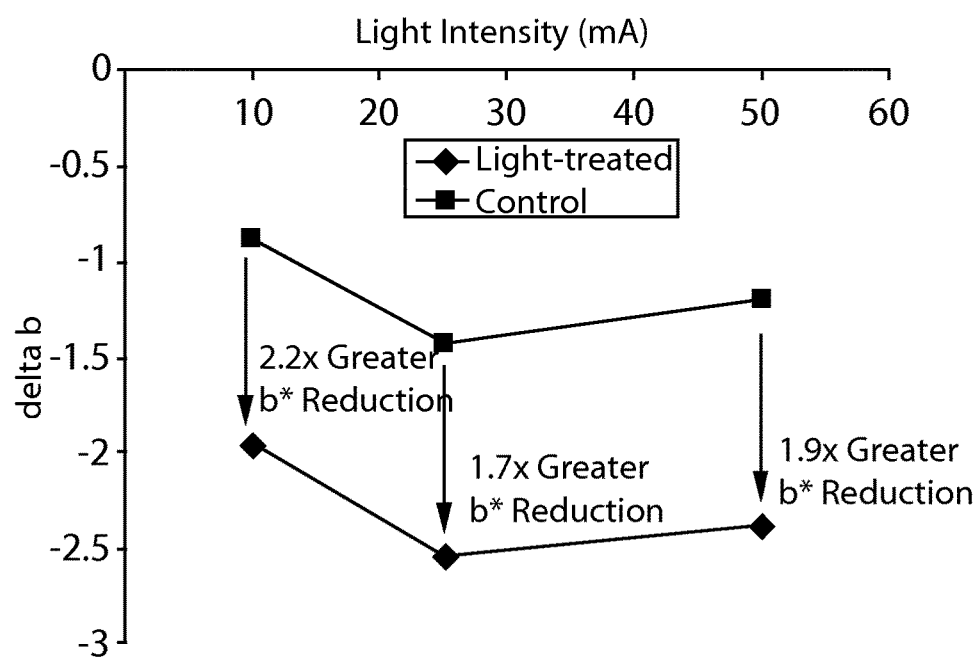
FIG. 7 is a graph illustrating the interplay between intensity of light radiation treatment and tooth whitening efficacy.

The differences in yellowness reduction (Δb*) between the varying light intensity enhanced treatments and the control (peroxide strip only) measurements at the end of treatment, expressed in percent improvement, are illustrated in the graph shown in FIG. 7.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

I claim:
1. A method of whitening teeth, comprising:
   applying a whitening composition as a layer having a thickness less than about 0.3 mm to at least one tooth;
   maintaining the whitening composition on the at least one tooth for a first time period without an application of light radiation; and
   after the first time period while the whitening composition remains upon the at least one tooth, directing a light radiation toward the at least one tooth for a second time period, the first time period having a duration greater than 50% of a total duration of the first and second time periods; and removing the whitening composition from the at least one tooth; wherein the whitening composition is translucent and is applied to said at least one tooth by a translucent strip or tray, and wherein said light radiation is directed toward said tooth through said translucent strip or tray and through said translucent whitening composition; and wherein the radiation intensity is no greater than about 150 mW/cm$^2$.

2. The method of claim 1, wherein the duration of the first time period is at least 80% of the total duration of the first and second time periods.

3. The method of claim 1, wherein the light radiation is selected for absorption by a stain on the at least one tooth by selecting a wavelength corresponding to a color substantially opposite a color of the stain on the 1976 CIE LAB color scale.

4. The method of claim 1, wherein the light radiation is provided at a wavelength between about 440 nm and about 490 nm.

5. The method of claim 1, wherein no photosensitizing agent is applied to the at least one tooth.

6. The method of claim 1, wherein the total duration of the first and second time periods is up to about 60 minutes, and the second time period is no greater than 5 minutes.

7. The method of claim 1, wherein the whitening composition comprises a layer that is applied to the tooth such that the whitening composition has a peroxide density less than about 1.3 mg/cm$^2$.

8. The method of claim 1, wherein the whitening composition comprises a peroxide active having a concentration between about 7.5% and about 20% of the whitening composition.

9. The method of claim 1, wherein the whitening composition is applied to the at least one tooth in a layer having a thickness less than about 0.2 mm.

10. The method of claim 1, wherein the whitening composition is provided on a strip of material configured to block light waves having a frequency of greater than about 700 nm.

11. The method of claim 1, further comprising maintaining the whitening composition on the at least one tooth for a third time period after the second time period.

12. The method of claim 1, wherein the tooth whitening composition does not include a photosensitizing agent.

13. A method of whitening teeth, consisting of:
applying a translucent whitening composition including a peroxide active having a concentration between about 7.5% and about 20% to at least one tooth in a layer having a thickness less than about 0.3 mm and a peroxide density less than about 1.3 mg/cm$^2$;
maintaining the whitening composition on the at least one tooth for a first time period of about 25 minutes to about 29.5 minutes without an application of light radiation; and
after the first time period, directing a light radiation provided at a wavelength between about 440 nm and about 490 nm and an intensity of no greater than about 45 mW/cm$^2$ toward the at least one tooth for a second time period of about 0.5 minutes to about 5 minutes while the whitening composition remains upon the at least one tooth;
and removing the whitening composition from the at least one tooth.

14. A method according to claim 13 wherein the translucent whitening composition is applied to said at least one tooth from a translucent strip, and the light radiation is directed onto said tooth through said translucent strip and through said translucent composition.

15. A method of whitening teeth, comprising:
applying a whitening composition as a layer having a thickness less than about 0.3 mm to at least one tooth;
maintaining the whitening composition on the at least one tooth for a first time period without an application of light radiation; and
after the first time period removing the whitening composition from the at least one tooth, and directing light radiation toward the at least one tooth for a second time period, the first time period having a duration greater than 50% of a total duration of the first and second time periods, wherein the radiation intensity is no greater than about 150 MW/cm$^2$.

16. The method of claim 15, wherein the duration of the first time period is at least 80% of the total duration of the first and second time periods.

17. The method of claim 15, wherein the light radiation is selected for absorption by a stain on the at least one tooth by selecting a wavelength corresponding to a color substantially opposite a color of the stain on the 1976 CIE LAB color scale.

18. The method of claim 15, wherein the light radiation is provided at a wavelength between about 440 nm and about 490 nm.

19. The method of claim 15, wherein no photosensitizing agent is applied to the at least one tooth.

20. The method of claim 15, wherein the whitening composition comprises a layer that is applied to the tooth such that the whitening composition has a peroxide density less than about 1.3 mg/cm$^2$.

21. The method of claim 20, wherein the whitening composition comprises a peroxide active having a concentration between about 7.5% and about 20% of the whitening composition.

22. The method of claim 21, wherein the whitening composition is applied to the at least one tooth from a strip, said composition being in a layer having a thickness less than about 0.2 mm.

23. The method of claim 22, wherein the total duration of the first and second time periods is up to about 60 minutes, and the second time period is no greater than 5 minutes.

24. A method of whitening teeth, consisting of:
applying a whitening composition including a peroxide active having a concentration between about 7.5% and about 20% to at least one tooth in a layer having a thickness less than about 0.3 mm and a peroxide density less than about 1.3 mg/cm$^2$;
maintaining the whitening composition on the at least one tooth for a first time period of about 25 minutes to about 29.5 minutes without an application of light radiation; and
after the first time period, removing said whitening composition and directing a light radiation provided at a wavelength between about 440 nm and about 490 nm and an intensity of no greater than about 45 mW/cm$^2$ toward the at least one tooth for a second time period of about 0.5 minutes to about 5 minutes.

25. A method according to claim 24 wherein the whitening composition is applied to said at least one tooth from a strip.

* * * * *